US011540777B2

(12) United States Patent
Lurvey (10) Patent No.: US 11,540,777 B2
(45) Date of Patent: Jan. 3, 2023

(54) REMOVABLE FLUID SENSOR IN AN ADMINISTRATION SET

(71) Applicants:Baxter International Inc., Deerfield, IL (US); BAXTER HEALTHCARE SA, Glattpark (CH)

(72) Inventor: Kent Lane Lurvey, Grayslake, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 946 days.

(21) Appl. No.: 16/373,281

(22) Filed: Apr. 2, 2019

(65) Prior Publication Data
US 2020/0315542 A1    Oct. 8, 2020

(51) Int. Cl.
| | | |
|---|---|---|
| *A61B 5/00* | (2006.01) | |
| *G01L 19/00* | (2006.01) | |
| *G01L 19/14* | (2006.01) | |
| *G01K 1/14* | (2021.01) | |
| *G01K 13/02* | (2021.01) | |
| *A61M 5/172* | (2006.01) | |

(Continued)

(52) U.S. Cl.
CPC ............. *A61B 5/6866* (2013.01); *A61B 5/01* (2013.01); *A61B 5/0215* (2013.01); *A61M 5/1723* (2013.01); *G01K 1/14* (2013.01); *G01K 13/02* (2013.01); *G01L 19/0023* (2013.01); *G01L 19/147* (2013.01); *A61M 2025/0003* (2013.01); *G01K 13/026* (2021.01)

(58) Field of Classification Search
CPC ........ A61M 1/3641; A61M 2025/0003; A61M 2205/3317; A61M 2205/3331; A61M 2205/3368; A61M 39/10; A61M 5/1723; A61B 5/01; A61B 5/0215; A61B 5/6866; G01L 19/0023; G01L 19/147
See application file for complete search history.

(56) References Cited

U.S. PATENT DOCUMENTS

| | | |
|---|---|---|
| 4,994,035 A | 2/1991 | Mokros |
| 5,096,385 A | 3/1992 | Georgi et al. |

(Continued)

FOREIGN PATENT DOCUMENTS

| | | |
|---|---|---|
| EP | 2383004 A1 | 11/2011 |
| EP | 2781234 A1 | 9/2014 |

(Continued)

OTHER PUBLICATIONS

Preliminary Report on Patentability for related International Application No. PCT/US2020/026165; action dated Oct. 14, 2021; (8 pages).

(Continued)

*Primary Examiner* — Andre J Allen
(74) *Attorney, Agent, or Firm* — K&L Gates LLP (57) ABSTRACT

Sensing systems, connectors, and methods include a housing, including a sensor and a locking mechanism, a junction, and a membrane. The junction includes a fluid inlet, a fluid outlet, and a receiving mechanism. The receiving mechanism is removably attachable to the locking mechanism. The membrane is disposed within the junction, and is in fluid communication with the fluid inlet and the fluid outlet. The sensor senses a property of a fluid across the membrane when the locking mechanism is attached to the receiving mechanism.

18 Claims, 5 Drawing Sheets

(51) Int. Cl.
*A61B 5/01* (2006.01)
*A61B 5/0215* (2006.01)
*A61M 25/00* (2006.01)

(56) References Cited

U.S. PATENT DOCUMENTS

| | | | |
|---|---|---|---|
| 6,358,225 B1 | 3/2002 | Butterfield | |
| 7,291,126 B2 | 11/2007 | Shekalim | |
| 7,744,573 B2 * | 6/2010 | Gordon | A61B 5/150824 604/32 |
| 8,313,468 B2 | 11/2012 | Geipel et al. | |
| 8,403,908 B2 | 3/2013 | Jacobson et al. | |
| 8,672,873 B2 | 3/2014 | Gravesen et al. | |
| 9,642,966 B2 | 5/2017 | Lee | |
| 2010/0056975 A1 * | 3/2010 | Dale | A61M 1/3609 604/6.16 |
| 2011/0046558 A1 * | 2/2011 | Gravesen | A61M 5/145 73/714 |
| 2014/0148757 A1 * | 5/2014 | Ambrosina | A61M 5/14224 604/67 |
| 2015/0273190 A1 | 10/2015 | Avevor | |
| 2016/0101278 A1 * | 4/2016 | Norris | A61M 39/22 604/29 |
| 2017/0059375 A1 | 3/2017 | Dekalb | |

FOREIGN PATENT DOCUMENTS

| | | | |
|---|---|---|---|
| JP | 2013226457 A * | 11/2013 | A61K 33/00 |
| WO | 02/03854 A2 | 1/2002 | |
| WO | 0203854 A2 | 1/2002 | |
| WO | 2009120240 A1 | 10/2009 | |
| WO | 2016/126856 A1 | 8/2016 | |

OTHER PUBLICATIONS

International Search Report and Written Opinion for related International Application No. PCT/US2020/026165; action dated Jun. 9, 2020; (14 pages).

* cited by examiner

REMOVABLE FLUID SENSOR IN AN ADMINISTRATION SET

BACKGROUND OF THE INVENTION

The present disclosure generally relates to fluid sensors for measuring various properties of fluid. More specifically, the present disclosure relates to methods, devices, and systems for administration sets, such as intravenous ("IV") administration sets with integrated sensor configuration hardware for removable fluid sensors.

In healthcare settings, vascular access to a patient may be required for numerous reasons, such as when undergoing monitoring, testing, diagnosis, and/or treatment. For example, an IV set may used in conjunction with an administration set during pump infusion or related drug delivery. Infusion may occur through either of a vein or an artery of the patient. Once infusion begins, additional patient monitoring is often desirable. For example, blood pressure monitoring devices may be implemented to measure patient blood pressure from the patient's vascular access, such as venous access. In this example, a dedicated IV fluid line may be implemented, for the sole purpose of in-line blood pressure monitoring of the patient. The dedicated line may include a pressure sensor having direct contact with fluid in the patient line. The sensor thus measures properties of the fluid in the fluid line.

Common difficulties with pressure sensing measurement include the requirement of adding a new dedicated line for pressure monitoring, leakage around the dedicated line, and potential disconnection of the line, all of which may have serious consequences for the patient. Additionally, monitoring systems require expensive and/or time consuming sterilization of the pressure sensor between uses or, in the alternative, may incur significant costs with single use disposable sensors. Further, placing a pressure sensing device in into a system capable of measuring IV pressure may require a skilled technician and substantial set up time, for example specifically related to IV insertion into the patient's arm.

SUMMARY

The present disclosure provides advantages and solutions to address current problems in existing patient monitoring technologies. In this regard, a sensor, such as a pressure sensor and related housing may be placed in contact with a thin membrane disposed along a fluid pathway of a patient fluid line. The sensor is thus placed in sensing communication with the thin membrane, to sense fluid parameters within the fluid pathway, such as pressure, temperature and/or other fluid parameters. The methods, devices, and systems disclosed herein provide an easy to use, multi-functional sensor and sensor housing that may be used with existing patient lines. The methods, devices, and systems provide for quick and easy connection and removal, while simultaneously ensuring sterility and a closed fluid system, such that the devices and systems may be used on multiple lines without requiring cleaning and sterilization. The devices and systems further allow for administration of a fluid to a patient while a fluid parameter is simultaneously being monitored.

In light of the disclosure herein, and without limiting the scope of the invention in any way, in a first aspect of the present disclosure, which may be combined with any other aspect listed herein unless specified otherwise, a sensing system includes a housing, a junction, and a membrane. The housing includes a sensor and a locking mechanism. The junction includes a fluid inlet, a fluid outlet, and a receiving mechanism. The receiving mechanism is removably attachable to the locking mechanism. The membrane is disposed within the junction, and is in fluid communication with the fluid inlet and the fluid outlet. The sensor senses a property of a fluid across the membrane when the locking mechanism is attached to the receiving mechanism.

In a second aspect of the present disclosure, which may be combined with any other aspect listed herein unless specified otherwise, the sensor is a pressure sensor.

In a third aspect of the present disclosure, which may be combined with any other aspect listed herein unless specified otherwise, the fluid inlet and the fluid outlet are connected to a fluid set, such that the fluid flows within the fluid set.

In a fourth aspect of the present disclosure, which may be combined with any other aspect listed herein unless specified otherwise, the fluid set is an intravenous line attached to a fluid source and a patient.

In a fifth aspect of the present disclosure, which may be combined with any other aspect listed herein unless specified otherwise, the sensor is not in direct fluid communication with the fluid set.

In a sixth aspect of the present disclosure, which may be combined with any other aspect listed herein unless specified otherwise, the fluid outlet comprises a Luer access device.

In a seventh aspect of the present disclosure, which may be combined with any other aspect listed herein unless specified otherwise, the sensor is removable from the housing while the housing is attached to the receiving mechanism.

In a eighth aspect of the present disclosure, which may be combined with any other aspect listed herein unless specified otherwise, the membrane ensures a fluid tight seal at the junction.

In a ninth aspect of the present disclosure, which may be combined with any other aspect listed herein unless specified otherwise, the fluid outlet is connected to a catheter.

In a tenth aspect of the present disclosure, which may be combined with any other aspect listed herein unless specified otherwise, the sensor is a temperature sensor.

In a eleventh aspect of the present disclosure, which may be combined with any other aspect listed herein unless specified otherwise, the locking mechanism is a spin lock collar.

In a twelfth aspect of the present disclosure, which may be combined with any other aspect listed herein unless specified otherwise, a connector includes a fluid inlet, a fluid outlet, a fluid path disposed between the fluid inlet and the fluid outlet, and a membrane. The membrane is disposed along the fluid path between the fluid inlet and the fluid outlet. The membrane is in fluid communication with the fluid path such that pressure signals from a fluid in the fluid path are transferred to the membrane.

In a thirteenth aspect of the present disclosure, which may be combined with any other aspect listed herein unless specified otherwise, a Luer access device is connected to the fluid inlet.

In a fourteenth aspect of the present disclosure, which may be combined with any other aspect listed herein unless specified otherwise, a catheter is connected to the fluid outlet.

In a fifteenth aspect of the present disclosure, which may be combined with any other aspect listed herein unless specified otherwise, the connector further includes a locking mechanism, such that a housing is attachable to the locking mechanism to place the sensor in sensing communication with the membrane.

In a sixteenth aspect of the present disclosure, which may be combined with any other aspect listed herein unless specified otherwise, the locking mechanism is a spin lock collar.

In a seventeenth aspect of the present disclosure, which may be combined with any other aspect listed herein unless specified otherwise, the locking mechanism is a lever lock.

In a eighteenth aspect of the present disclosure, which may be combined with any other aspect listed herein unless specified otherwise, the fluid inlet is in fluid communication with an intravenous line, arterial line, or a catheter that is connected to a patient's vascular system.

In a nineteenth aspect of the present disclosure, which may be combined with any other aspect listed herein unless specified otherwise, the fluid inlet is capped, such that the fluid outlet is directly measuring a pressure only through the fluid outlet.

In a twentieth aspect of the present disclosure, which may be combined with any other aspect listed herein unless specified otherwise, a method for sensing a blood parameter includes placing a sensor in a sensor housing. The method further includes allowing a fluid to flow along a fluid path from a fluid inlet to a fluid outlet. A membrane is disposed between the fluid inlet and the fluid outlet. The membrane is in fluid communication with the fluid path, such that pressure signals from the fluid in the fluid path are transferred to the membrane. The method further includes contacting the sensor with the membrane. The method then includes measuring, via the sensor, a sensed parameter of the fluid across the membrane.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not necessarily have to have all of the advantages listed herein. Moreover, it should be noted that the language used in the specification has been selected for readability and instructional purposes, and not to limit the scope of the inventive subject matter.

BRIEF DESCRIPTION OF THE FIGURES

Understanding that figures depict only typical embodiments of the invention and are not to be considered to be limiting the scope of the present disclosure, the present disclosure is described and explained with additional specificity and detail through the use of the accompanying figures. The figures are listed below.

DETAILED DESCRIPTION OF EXAMPLE EMBODIMENTS

Detailed embodiments of devices and methods are disclosed herein. However, it is to be understood that the disclosed embodiments are merely exemplary of the devices and methods, which may be embodied in various forms. Therefore, specific functional details disclosed herein are not to be interpreted as limiting, but merely as a basis for the claims as a representative example for teaching one skilled in the art to variously employ the present disclosure.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Figure 1:
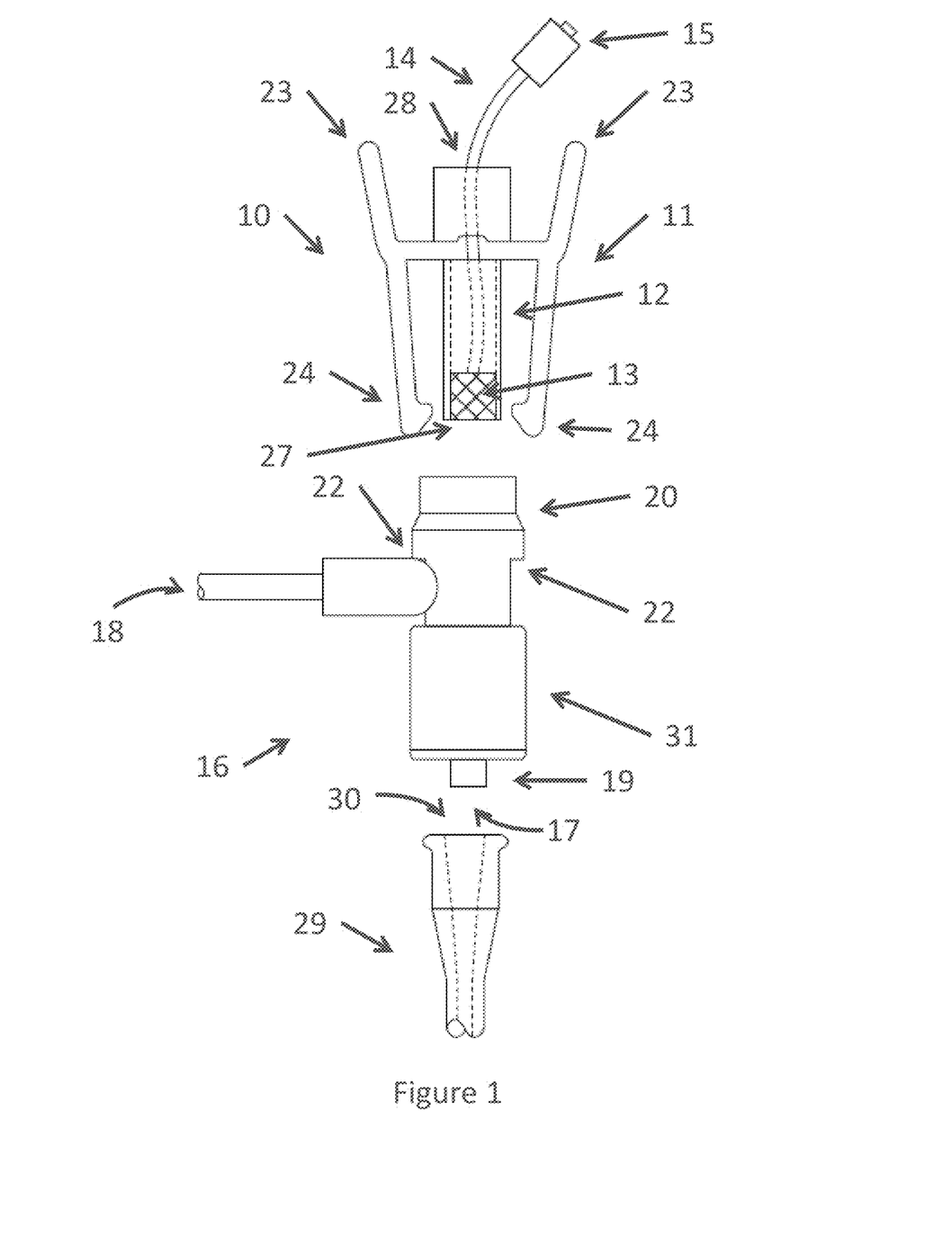
FIG. 1 illustrates an exterior side view of an embodiment of a sensor housing, a T-housing, a sensor configured for connection, and a catheter, according to the present disclosure.

Referring now to the figures, FIG. 1 generally illustrates a side view of an embodiment of a sensor housing 10 and a T-housing 16. Generally, the sensor housing 10 may be removably connectable to the T-housing 16 as disclosed in greater detail herein. When the sensor housing 10 is connected to the T-housing 16, a sensor 13 disposed within sensor housing 10 may sense a fluid parameter of a fluid flowing through the T-housing 16. In various embodiments, the sensor housing 10 and the T-housing 16 may be constructed of any suitable plastic or rubber material, such as polyvinyl chloride ("PVC"), non-DEHP PVC, Acrylic, ABS, Krayton polypropylene mixture, co-polyester blends or other similar materials.

Generally, the sensor housing 10 may include a lock housing 11 and a central sensor housing 12. The lock housing 11 may be disposed concentrically around the central sensor housing 12. The lock housing 11 is provided to removably attach the sensor housing 10 to the T-housing 16. More specifically, lock housing 11 includes lock housing upper arms 23 and lock housing lower arms 24. The lock housing upper arms 23 may be connected to the lock housing lower arms 24, and be placed on opposite ends of the lock housing 11. Lock housing lower arms 24 are configured to separate and pivot outward, such as away from central sensor housing 12, when the lock housing upper arms 23 are brought toward one another, such as when pinched by a user. It should be appreciated that lock housing 11 is constructed of a material with an appropriate modulus of elasticity to allow for a degree of flexibility for pivoting purposes. In an embodiment, lock housing 11, including lock housing upper arms 23 and lock housing lower arms 24 is a single-piece structure, formed via injection molding, 3D molding, or other related processes.

In related embodiments, sensor housing 10 may include a screw configuration and/or spin collar. In a screw configuration, the sensor housing 10 includes threads engagable to opposing threads on the T-housing 16, such that the sensor housing 10 may screw onto the T-housing 16 directly. For example, threaded engagement may replace the lock housing lower arms 24 engagement described in greater detail herein. Likewise, in the spin collar configuration, a spin collar may be provided on the sensor housing 10, the central sensor housing 12, and/or the T-housing 16 to connect the sensor housing 10 to the T-housing 16.

Central sensor housing 12 of sensor housing 10 may receive sensor 13. For example, the central sensor housing 12 may include a central sensor housing contact end 27 and a central sensor housing electrical lead end 28; the sensor 13 may be placed into the central sensor housing 12 through the central sensor housing electrical lead end 28, such that sensor 13 abuts the central sensor housing contact end 27. The central sensor housing contact end 27 may include a hole or cut-out, such that a portion of sensor 13 is flush with or, alternatively, extends beyond central sensor housing contact end 27. Sensor 13 may engage with central sensor housing contact end 27 via adhesive, hook and loop fasteners, snap fit, interference fit, or any other related means for mechanically securing sensor 13 to central sensor housing contact end 27.

Sensor 13 may further include a sensor line 14 in electronic communication with the sensor 13 and with an electrical connector 15. In a primary embodiment, sensor 13 is a pressure sensor, such as a piezo-electric transducer. Thus, sensor 13 communicates pressure readings via sensor line 14 to electrical connector 15. In alternate embodiments, the sensor 13 is another type of sensor, such as a temperature sensor, an electrical sensor, an inductive sensor, a capacitive sensor, an electrolytic sensor, or any other sensor for detecting a property of a fluid.

The sensor 13 is generally configured to convert a sensed value, for example a sensed pressure or temperature, to an electronic signal that is communicated via sensor line 14 to the electrical connector 15. It should be appreciated that, while certain embodiments disclosed herein specifically relate to measured pressure, sensor 13 may measure any number of other fluid parameters. The electrical connector 15 may be connected to a transmitter, configured to send the sensed pressure to an external device, such as an external processor, monitor, and/or computing device. For example, the electrical connector 15 may be connected to a Bluetooth® device that transmits the sensed pressure to a remote location. In a different embodiment, sensor 13 includes an internal transmitter, such that no sensor line 14 or electrical connector 15 is required. In another different embodiment, the electrical connector 15 is physically connected to an external device, for example a blood pressure monitoring system, patient monitoring system, and/or other medical device that evaluates sensed patient parameters.

Continuing on, the T-housing 16 includes three distinct protrusions: a sensor receiving portion 20, a fluid path inlet 18, and a fluid path outlet 19. In some embodiments, the fluid path inlet 18 and/or the fluid path outlet 19 are Luer connectors. As shown in FIG. 1, the sensor receiving portion 20 and the fluid path outlet 19 are on opposite ends of the T-housing 16. The fluid path inlet 18 is configured perpendicular to a vector defined by the sensor receiving portion 20 and the fluid path outlet 19. However, it should be appreciated that the three protrusions may be reoriented as required for an application. For example, the fluid path outlet 19 and the fluid path inlet 18 may be on opposite ends of the T-housing 16, and the sensor receiving portion 20 may be positioned at any angle from the fluid path outlet 19, such as 90 degrees, 60, degrees, 45 degrees, or any other angle.

The T-housing 16 includes housing fastener members 22, which are protrusions configured to receive the lock housing lower arms 24, such that the lock housing lower arms 24 engage the housing fastener members 22. Specifically, as previously noted, the user may connect the sensor housing 10 to the T-housing 16 by pinching the lock housing upper arms 23 together. Pinching the lock housing upper arms 23 together separates the lock housing lower arms 24. The sensor housing 10 is placed in communication with the T-housing 16, such that the lock housing lower arms 24 are concentric around the housing fastener members 22. The lock housing upper arms 23 are released, resulting in the lock housing lower arms 24 springing back to a pre-pinched orientation, thereby coupling the lock housing lower arms 24 with the housing fastener members 22. As previously noted, in alternate embodiments locking arms may be eliminated and replaced with a spin collar or threaded connection.

Figure 2:
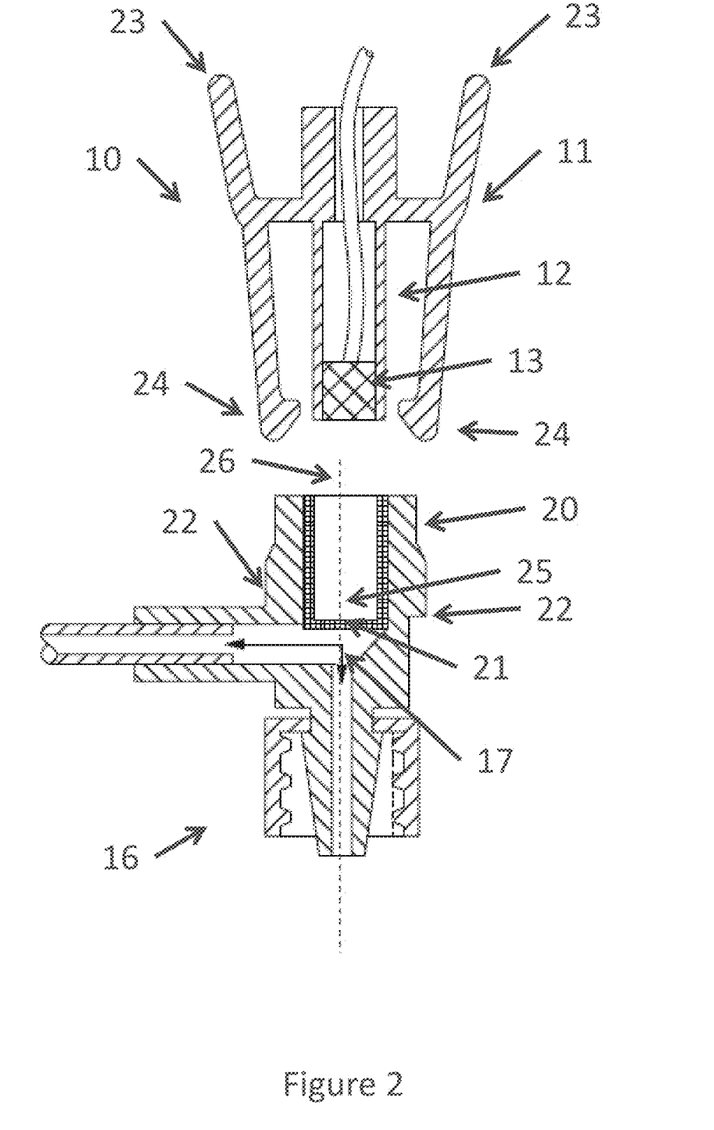
FIG. 2 illustrates a cutaway cross-sectional view of an embodiment of a sensor housing, a T-housing, a sensor configured for connection, and a catheter, according to the present disclosure.

Referring now to FIG. 2, the sensor receiving portion 20 includes a sensor receiving portion cavity 25. The sensor receiving portion cavity 25 is generally configured to concentrically receive the central sensor housing 12. Specifically, when the sensor housing 10 is connected to the T-housing 16, the central sensor housing 12 is disposed within the sensor receiving portion cavity 25, such that the central sensor housing contact end 27 abuts a membrane 21. In an embodiment, the sensor 13 sits flush against the central sensor housing 12. The housing fastener members 22 receive the lock housing lower arms 24 when the central sensor housing contact end 27 abuts the membrane 21, to retain central sensor housing contact end 27 and sensor 13 against the membrane 21.

A fluid pathway 17 is defined from the fluid path inlet 18, into the T-housing 16, and through the fluid path outlet 19. A fluid may travel in either direction through the fluid pathway 17. Either or both of the fluid path inlet 18 and the fluid path outlet 19 may be coupled to a fluid line connected to a patient and/or a connector. In a particular example, fluid path inlet 18 is connected, via patient tubing, to a fluid source such as an IV bag; fluid path outlet 19 is connected, via patient tubing, to an IV catheter inserted into the arm of a patient. The membrane 21 is disposed along the fluid pathway 17, such that the membrane 21 is in fluid contact with the fluid pathway 17. The membrane 21 is fluid tight, such that no leaks from the fluid pathway 17 at membrane 21 would occur.

The membrane 21 includes a fluid side and a non-fluid side. The fluid side of the membrane 21 directly contacts fluid within the fluid pathway 17. The non-fluid side of the membrane 21 defines at least a portion of the sensor receiving portion cavity 25. In an embodiment, the entire sensor receiving portion cavity 25 comprises the membrane 21. When the sensor housing 10 is connected to the T-housing 16, the central sensor housing contact end 27 contacts the non-fluid side of the membrane 21. Sensor 13 is thus in direct contact with membrane 21 via the central sensor housing contact end 27.

A fluid parameter of the fluid within the fluid pathway 17, for example a pressure or a temperature of the fluid, may therefore be sensed by the sensor 13 across membrane 21. In an embodiment, the membrane 21 is highly pliable and able to transmit variations of pressure between a fluid side of the membrane 21 and a non-fluid side of the membrane 21 in contact with the sensor 13. In an embodiment, a sensing portion of the sensor 13 is integrated into the central sensor housing contact end 27, such that sensor 13 may sense the fluid parameter by directly contacting the membrane 21. In an embodiment, the membrane 21 is sufficiently thin to allow a sensed parameter, such as pressure, to be communicated from the fluid in the fluid pathway 17, through the membrane 21. In an embodiment, the membrane 21 is a flexible elastomeric diaphragm. In an alternate embodiment, the membrane 21 is a thin film. Additionally or alternatively, the membrane or film may reside in the housing 27 allowing for the T-housing to have an elastomeric septum.

Via the system described above, sensor 13 is able to sense a fluid parameter within fluid pathway 17, through the membrane 21, while remaining sterilely separated from the fluid itself. Such a configuration may allow for the sensor 13 to be reused across multiple readings and/or patient lines and without requiring cleaning and/or sterilization of the sensor 13, because the sensor 13 only contacts the membrane 13 and does not contact fluid in the fluid pathway 17. This configuration further reduces the risk of accidental disconnection of a patient line, unsecure connection to a patient line, bleed out from the catheter, and/or misidentification of a required sensing site because the sensor housing 10 must only clip, snap, screw, or otherwise connect to the T-housing 16. Accordingly, if the sensor housing 10 is not placed properly, becomes disconnected, is connected to an incorrect location, and/or is otherwise improperly placed, the fluid pathway 17 is not compromised. In addition, should the sensor 13 fail, there may be no interruption of other critical infusion processes because the sensor 13 and the sensor housing 10 may be removed and/or replaced without any direct effect on the fluid pathway 17. Providing the T-housing 16 with a sensor receiving portion 20 may reduce time needed to connect the sensor 13, as the housing 10 only need be connected to the T-housing 16 to provide sensing capability.

In an embodiment, the fluid path outlet 19 may include a male Luer connection. In such an embodiment, the fluid path outlet 19 may be connectable to a catheter 29. For example, the catheter 29 may include a female Luer 30; the female Luer 30 may be connectable to the male Luer of the fluid path outlet 19. In an embodiment, a fluid within the fluid pathway 17 may flow through the fluid path outlet 19 and into the catheter 29 by flowing through the female Luer 30.

In an embodiment, the T-housing 16 may include a spin lock collar 31. The spin lock collar 31 may engage the catheter 29. In an embodiment, a collar of the spin lock collar 31 may engage a portion of the catheter 29 when the female Luer 30 is connected to the fluid path outlet 19. In an embodiment where the collar of the spin lock collar 31 engages the catheter 29, the spin lock collar 31 may ensure a tight connection between the female Luer 30 and the fluid path outlet 29 so that a fluid flowing through the fluid path outlet 19 and into the catheter 29 by flowing through the female Luer 30 does not leak through the connection between the female Luer 30 and the fluid path outlet 19.

FIG. 2 generally illustrates a cutaway view of an embodiment of the sensor housing 10, the T-housing 16, and the sensor 13 configured for connection. A centerline 26 is shown in FIG. 2. The centerline 26 may pass through the centerline of the generally circular sensor receiving portion 20 and the generally circular sensor receiving portion cavity 25. The central sensor housing 12 of the sensor housing 10 may also be generally circular in shape.

For attachment, sensor 13 is placed within the central sensor housing 12 of the sensor housing 10. Alternatively, sensor 13 is pre-disposed within or permanently affixed to central housing 12. The lock housing upper arms 23 are pinched by the user, separating the lock housing lower arms 24. The central sensor housing 12 is aligned with the sensor receiving portion cavity 25, and subsequently inserted into the sensor receiving portion cavity 25 until the lock housing lower arms 24 engage the housing fastening members 22. The lock housing upper arms 23 are then released by the user. In this locked configuration, the sensor 13 contacts membrane 21, which is in fluid contact with a fluid in fluid pathway 17. Thus, sensor 13 may sense a parameter of the fluid flowing within in the fluid pathway 17 across membrane 21, such as fluid pressure.

Figure 3:
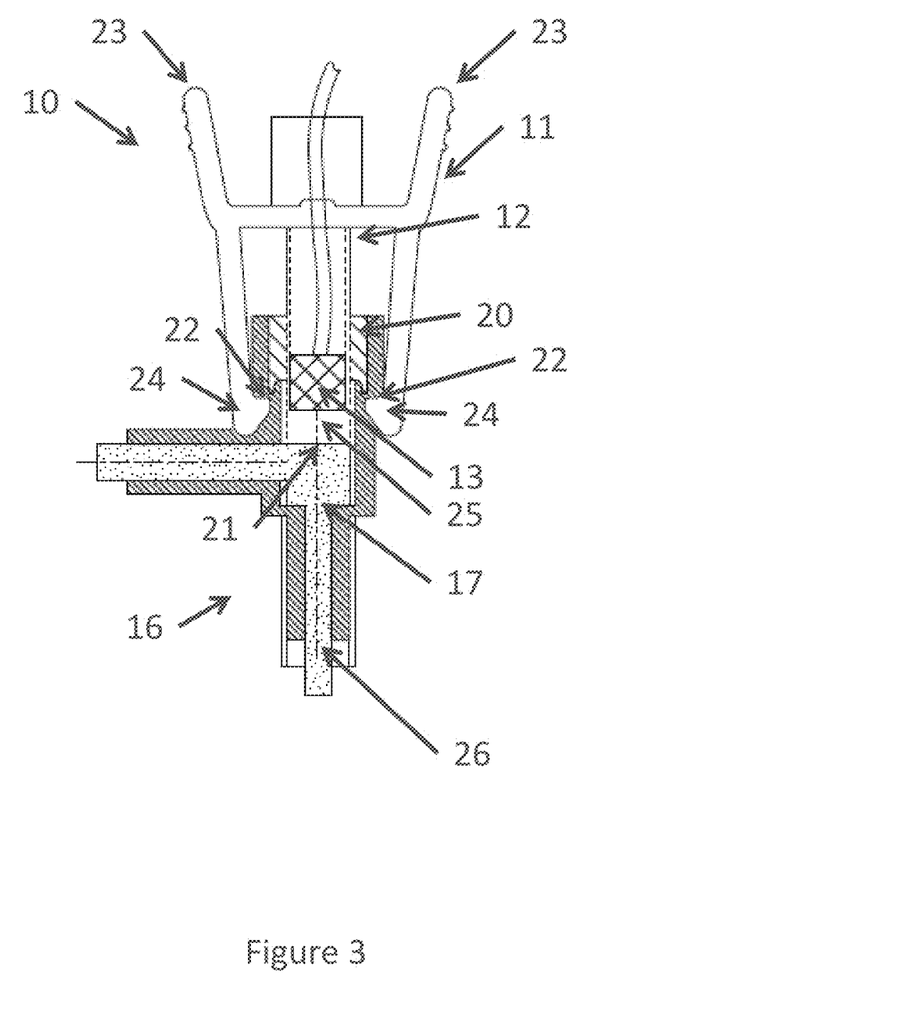
FIG. 3 illustrates a cutaway view of an embodiment of a sensor housing, a T-housing, and a sensor in an assembled connection state, according to the present disclosure.

FIG. 3 generally illustrates a cutaway view of an embodiment of the sensor housing 10, the T-housing 16, and the sensor 13 in an assembled configuration. As shown, the lock housing upper arms 23 are not pinched, which ensures that lock housing lower arms 24 engage the housing fastening members 22. The central sensor housing 12 of the sensor housing 10 is aligned substantially along the centerline 26. When the lock housing lower arms 24 engage the housing fastening members 22, the central sensor housing 12 is fully inserted and locked into the sensor receiving portion cavity 25 such that the central sensor housing 12 contacts the membrane 21. When the central sensor housing 12 contacts the membrane 21, the sensor 13 may acquire measurement readings across the membrane 21.

In an embodiment, the sensor 13 may be removable from the central sensor housing 12 of the sensor housing 10 without disengaging the lock housing 11. For example, sensor 13 may be removed, replaced, reoriented, and/or otherwise moved out of contact with the membrane 21 in the central sensor housing 12 without disengaging the sensor housing 10 from the T-housing 16. As shown in FIG. 3, the sensor 13 is not flush against the central sensor housing 12 as compared to the position of the sensor 13 relative to the central sensor housing 12 of FIGS. 1 and 2.

While the T-housing 16 is illustrated as a standalone component in FIGS. 1 to 3, the T-housing 16 may be provided as an extension of a catheter hub or placed at or near the catheter hub, part of an extension set, and/or part of an administration set used to access a cardiovascular system of a patient. In an embodiment, the fluid path inlet 18 is capped. In an embodiment, a Luer access device or a female Luer hub allowing access to another connected set or Luer connector may be attached to the T-housing 16, for example to the fluid path inlet 18 in place of the IV set tubing. In such an embodiment, the T-housing 16 may be used with the Luer access device to provide access to the fluid pathway 17. In an embodiment, an attachment to the Luer access device may be made with an Interlink® T-housing. In an embodiment, the T-housing 16 may provide for elastomeric access, for example an Interlink® septum, to contain fluid flow in the fluid pathway 17. In an embodiment, an opening of the T-housing 16, for example the fluid path outlet 19, may be used to administer fluids with or without the sensor housing 10 and/or the sensor 13 connected to the T-housing 16. In various embodiments, the T-housing 16 may further include check valves, flow restrictors, and/or other components configured to enhance system performance related to fluid flow.

Figure 4:
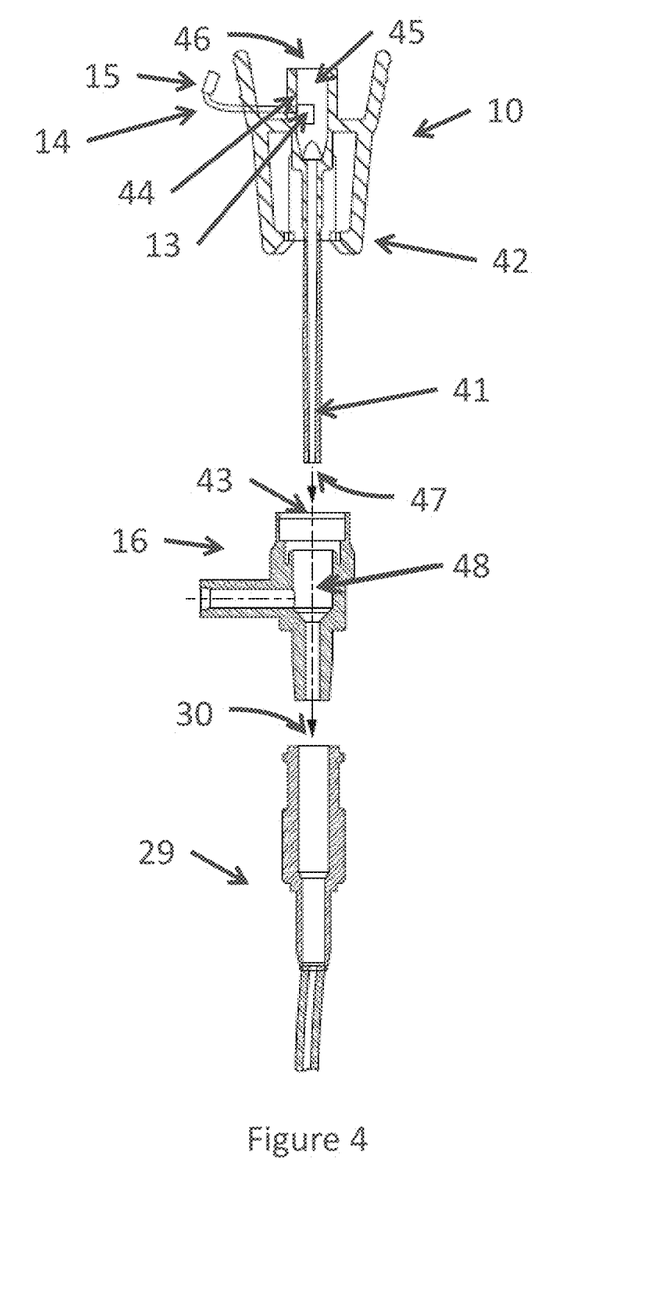
FIG. 4 illustrates a cutaway view of an embodiment of an alternative sensor housing integrated with a small orifice connector, a T-housing, a catheter, and a sensor, according to the present disclosure.

FIG. 4 illustrates a cutaway view of an embodiment of an alternative sensor housing integrated with a small orifice connector, for example a long cannula tube extension 41, the T-housing 16, the catheter 29, and the sensor 13. The sensor housing 10 may include a lever lock configuration 42, which is generally described above in regard to FIG. 1. Referring again to FIG. 4, the sensor housing 10 may include a lever lock sidewall 44. The lever lock sidewall 44 may include any portion of the sensor housing 10 that defines a flow path 45 through the sensor housing 10. The sensor housing 10 may be assembled as a single component, or in the alternative be an assembly including multiple components in a removable and/or permanently affixed state.

The flow path 45 may be defined by a central portion of the sensor housing 10 and may include a sensor housing inlet 46 and a sensor housing outlet 47. The sensor housing 10 may be integrated with and/or include the long cannula tube extension 41. The sensor housing outlet 47 may be positioned at an end of the long cannula tube extension 41. The long cannula tube extension 41 may be a capillary tube.

In an embodiment, the sensor 13 may be integrated into the lever lock sidewall 44. For example, the sensor 13 may be assembled into the lever lock sidewall 44 and/or be insert molded into the lever lock sidewall 44. In an embodiment, the sensor 13 may be solvent bonded to the lever lock sidewall 44. While the sensor 13 is shown in a single position in FIG. 4, it should be appreciated that the sensor 13 may be located at any other location along the flow path 45 of the sensor housing 10. In other embodiments, the lever lock sidewall 44 may include a hole. The hole may allow fluid in the flow path 45 to contact the sensor 13 for reading. In such an embodiment, the sensor 13 may need to be bonded and/or affixed to the lever lock sidewall 44 to ensure a tight, non-leaking seal between the sensor 13 and the lever lock sidewall 44.

The sensor 13 may be reusable and/or replaceable within the sensor housing 10. In an embodiment, the sensor 13 is not removable from the sensor housing 10. The sensor 13 may include the sensor line 14 and the electrical connection 15 to communicate a signal received by the sensor 13 to a control unit and/or other input receiving device as previously disclosed. In an embodiment, the sensor housing 10 is a standalone component. In alternative embodiments, the sensor housing 10 may be part of an extension set and/or an administration set. While only the sensor housing 10 shown herein is a male sensor housing 10, the sensor housing 10 may instead be a female end adapted to be used with a male adapted.

In an embodiment, the sensor housing 10 includes the long cannula tube extension 41, configured to access the catheter 29 through the female Luer 30 of the catheter 29. The catheter may provide access to a patient's vascular system. The long cannula tube extension 41 may be configured to connect to the catheter 29 after passing through the T-housing 16. For example, the long cannula tube extension 41 may be configured to pass through a T-housing cavity 48 of the T-housing 16 and extend into the catheter 29. The T-housing 16 may optionally include a slit septum 43. The slit septum 43 may provide sealing access to the T-housing 16.

Figure 5:
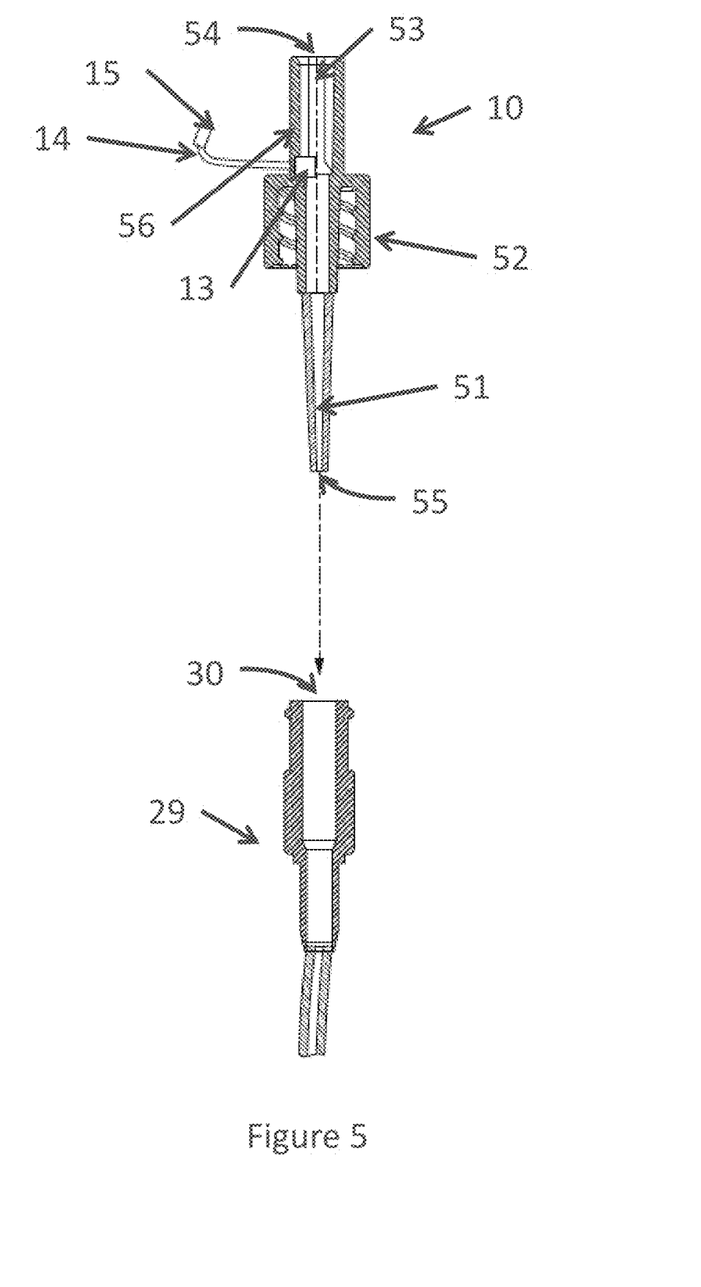
FIG. 5 illustrates a cutaway view of an embodiment of an alternative sensor housing integrated with a small orifice connector, a catheter, and a sensor, according to the present disclosure.

FIG. 5 illustrates a cutaway view of an embodiment of an alternative sensor housing 10 integrated with a small orifice connector, for example a long cannula tube extension 51, the catheter 29, and the sensor 13. The sensor housing 10 may include a male Luer connection 52 instead of the lever lock configuration 42 of FIG. 4. Referring again to FIG. 5, the sensor housing 10 may include a male Luer sidewall 56. The male Luer sidewall 56 may include the sensor 13. The sensor 13 may be connected to a controller and/or other input receiving device via sensor line 14 and/or electrical connector 15.

The sensor 13 may be integrated into the male Luer sidewall 56 to sense fluid in a flow path 53 within the sensor housing 10. In a preferred embodiment, the sensor 13 does not directly contact a fluid within the flow path 53 of the sensor housing 10. The sensor 13 may be assembled or otherwise embedded into the male Luer sidewall 56 and/or be insert molded into the male Luer sidewall 56.

In an embodiment that is insert molded, the sensor 13 may be added to a pre-molded sensor housing 10 with electrical leads leading out from the pre-molded sensor housing 10. Then, the sensor housing 10 may be radio frequency bonded, solvent-adhesive bonded, and/or snap-fitted to a female Luer adapter. In other embodiments, the sensor housing 10 is radio frequency bonded, solvent-adhesive bonded, and/or snap-fitted to a male Luer adapter. Two shot molding may be used to attach the transducer to the sensor housing 10.

In an embodiment, the flow path 53 includes a sensor housing inlet 54 and a sensor housing outlet 55. The sensor housing outlet 55 may be positioned on an end of the long cannula tube extension 51. In some embodiments, the long cannula tube extension 51 is not included.

The male Luer connection 52 may optionally connect to the female Luer 30 of the catheter 29 without first passing through the T-housing 16. For example, in FIG. 5 the male Luer connection 52 is configured to connect directly to the female Luer 30 without any intervening structure. In such an embodiment, a fluid may flow to and/or from the sensor housing 10 and the catheter 29 without passing through any intervening structure. In other embodiments, the embodiment according to FIG. 5 may include the T-housing 16.

A configuration according to FIG. 5 without the T-housing 16 may enable a sensor to sense a more accurate and precise reading, such as a pressure reading, because there is less intervening structure between sensor 13 and the fluid. Additionally or alternatively, the configuration according to FIG. 5 may allow for fluid to be delivered at the same time that a reading is being measured by the sensor 13. For example, any negative effects created by a small diameter fluid column as a result of the long cannula tube extension 51 may be mitigated through positioning the sensor 13 closer to the proximity of the catheter, which is closer to a patient's vascular blood pressure.

Generally, it should be reiterated that sensor 13 is not, in any way, limited to a blood pressure sensor. As a pressure sensor, sensor 13 can measure a number of additional or alternate physiological parameters such as hydrodynamic condition, blood element parameters, heart beat, respiration, fluid status via peripheral venous waveform analysis, or other related parameters. Likewise, because sensor 13 is not limited to pressure measurements, alternate sensor technology could be implemented, for example, to measure temperature, acoustics such as heart beat and heart murmur, electrical characteristics such as EKG and bioimpedance, electrolytic characteristics such as glucose levels, blood gas, and/or low flow rate occlusion to identify IV infiltration or access disconnection, or the like.

It should be understood that various changes and modifications to the examples described here will be apparent to those skilled in the art. Such changes and modifications can be made without departing from the spirit and scope of the present subject matter and without diminishing its intended advantages. It is therefore intended that such changes and modifications be covered by the appended claims. Further, the present embodiments are thus not to be limited to the precise details of methodology or construction set forth above as such variations and modification are intended to be included within the scope of the present disclosure. Moreover, unless specifically stated any use of the terms first, second, etc. do not denote any order or importance, but rather the terms first, second, etc. are merely used to distinguish one element from another.

What is claimed is:

1. A sensing system comprising:
   a housing, the housing including a sensor and a locking mechanism, wherein the locking mechanism includes upper arms and lower arms, and wherein the upper arms are configured to be pinched by a user;
   a junction, the junction including a fluid inlet, a fluid outlet, and a receiving mechanism, the receiving mechanism removably attachable to the locking mechanism; and
   a membrane disposed within the junction, the membrane in fluid communication with the fluid inlet and the fluid outlet,
   wherein the sensor senses a property of a fluid across the membrane when the locking mechanism is attached to the receiving mechanism.

2. The system according to claim 1, wherein the sensor is a pressure sensor.

3. The system according to claim 1, wherein the fluid inlet and the fluid outlet are connected to a fluid set, such that the fluid flows within the fluid set.

4. The system according to claim 3, wherein the fluid set is an intravenous line attached to a fluid source and a patient.

5. The system according to claim 3, wherein the sensor is not in direct fluid communication with the fluid set.

6. The system according to claim 1, wherein the fluid outlet comprises a Luer access device.

7. The system according to claim 1, wherein the sensor is removable from the housing while the housing is attached to the receiving mechanism.

8. The system according to claim 1, wherein the membrane ensures a fluid tight seal at the junction.

9. The system according to claim 1, wherein the fluid outlet is connected to a catheter.

10. The system according to claim 1, wherein the sensor is a temperature sensor.

11. A connector comprising:
    a fluid inlet;
    a fluid outlet;
    a fluid path, the fluid path disposed between the fluid inlet and the fluid outlet; and
    a membrane, the membrane disposed along the fluid path between the fluid inlet and the fluid outlet, wherein the membrane is in fluid communication with the fluid path such that pressure signals from a fluid in the fluid path are transferred to the membrane, and wherein a sensor is disposed adjacent to the membrane via a locking mechanism having upper arms and lower arms, such that the upper arms are configured to be pinched by a user;
    a junction, the junction including a fluid inlet, a fluid outlet, and a receiving mechanism, the receiving mechanism removably attachable to the locking mechanism; and
    a membrane disposed within the junction, the membrane in fluid communication with the fluid inlet and the fluid outlet,
    wherein the sensor senses a property of a fluid across the membrane when the locking mechanism is attached to the receiving mechanism.

12. The connector according to claim 11, further comprising a Luer access device connected to the fluid inlet.

13. The connector according to claim 11, further comprising a catheter connected to the fluid outlet.

14. The connector according to claim 11, wherein a housing is attachable to the locking mechanism to place a sensor in sensing communication with the membrane.

15. The connector according to claim 14, wherein the locking mechanism is a lever lock.

16. The connector according to claim 11, wherein the fluid outlet is in fluid communication with an intravenous line, arterial line, or a catheter that is connected to a patient's vascular system.

17. The connector according to claim 11, wherein the fluid inlet is capped, such that the fluid outlet is directly measuring a pressure only through the fluid outlet.

18. A method for sensing a blood parameter, the method comprising:
    placing a sensor in a sensor housing;
    allowing a fluid to flow along a fluid path from a fluid inlet to a fluid outlet, wherein a membrane is disposed between the fluid inlet and the fluid outlet, the membrane in fluid communication with the fluid path such that pressure signals from the fluid in the fluid path are transferred to the membrane;
    contacting the sensor with the membrane via a locking mechanism having upper arms and lower arms, such that the upper arms are configured to be pinched by a user;
    measuring, via the sensor, a sensed parameter of the fluid across the membrane.

* * * * *